(12) United States Patent
Hansson et al.

(10) Patent No.: US 8,324,444 B2
(45) Date of Patent: Dec. 4, 2012

(54) ABSORBENT ARTICLES AND LAMINATES CONTAINING A BONDING PATTERN

(75) Inventors: Morgan Hansson, Göteborg (SE); Robert Torstensson, Göteborg (SE); Henrik Carlén, Västra Frölunda (SE)

(73) Assignee: SCA Hygiene Products AB, Gothenburg (SE)

( * ) Notice: Subject to any disclaimer, the term of this patent is extended or adjusted under 35 U.S.C. 154(b) by 834 days.

(21) Appl. No.: 12/064,221

(22) PCT Filed: Sep. 13, 2005

(86) PCT No.: PCT/SE2005/001321
§ 371 (c)(1),
(2), (4) Date: Feb. 19, 2008

(87) PCT Pub. No.: WO2007/032710
PCT Pub. Date: Mar. 22, 2007

(65) Prior Publication Data
US 2008/0269704 A1 Oct. 30, 2008

(51) Int. Cl.
*A61F 13/15* (2006.01)
(52) U.S. Cl. .......... 604/361; 604/365; 604/367
(58) Field of Classification Search .......... 604/361, 604/365, 367
See application file for complete search history.

(56) References Cited

U.S. PATENT DOCUMENTS

| | | | |
|---|---|---|---|
| 3,616,898 A | 11/1971 | Massie | |
| 3,723,174 A | 3/1973 | Swanson et al. | |
| 4,681,791 A | 7/1987 | Shibahashi et al. | |
| 4,792,487 A | 12/1988 | Schubring et al. | |
| 4,826,550 A | 5/1989 | Shimizu et al. | |
| 5,133,707 A * | 7/1992 | Rogers et al. | 604/389 |
| 5,167,652 A | 12/1992 | Mueller | |
| 5,197,958 A | 3/1993 | Howell | |
| 5,897,541 A * | 4/1999 | Uitenbroek et al. | 604/358 |
| 6,228,804 B1 | 5/2001 | Nakashima | |
| 6,352,528 B1 * | 3/2002 | Weber et al. | 604/385.03 |
| 6,719,742 B1 * | 4/2004 | McCormack et al. | 604/385.01 |
| 7,241,627 B2 * | 7/2007 | Wilhelm et al. | 436/518 |
| 2003/0087566 A1 | 5/2003 | Carlyle et al. | |
| 2003/0114809 A1 | 6/2003 | Gagliardi et al. | |
| 2005/0048856 A1 * | 3/2005 | Hauser et al. | 442/59 |

(Continued)

FOREIGN PATENT DOCUMENTS

EP 0 347 657 A2 12/1989

(Continued)

OTHER PUBLICATIONS

Form PCT/ISA/210 (International Search Report) dated Mar. 17, 2006.

(Continued)

*Primary Examiner* — Lynne Anderson
(74) *Attorney, Agent, or Firm* — Buchanan Ingersoll & Rooney PC

(57) ABSTRACT

An absorbent article, such as a diaper, a pant diaper, a sanitary napkin, an incontinence guard etc., includes components that are joined together by a bonding pattern. The bonding pattern has color-changing properties triggered by heat and/or pressure exerted during the bonding process, the color-changing properties being either irreversible or reversible. The color-changing properties may be accomplished by thermochromic pigments, thermochromic fibers and/or pressure-sensitive pigments. A laminate is formed from two or more web material layers joined together by a bonding pattern having color-changing.

17 Claims, 3 Drawing Sheets

U.S. PATENT DOCUMENTS

| | | | |
|---|---|---|---|
| 2005/0124947 A1* | 6/2005 | Fernfors | 604/361 |
| 2006/0025739 A1* | 2/2006 | DiPalma et al. | 604/385.02 |

FOREIGN PATENT DOCUMENTS

| | | |
|---|---|---|
| EP | 1 035 818 B1 | 9/2000 |
| EP | 1 314 802 A2 | 5/2003 |
| EP | 1 327 427 A1 | 7/2003 |
| EP | 1 591 131 A1 | 11/2005 |
| JP | 63-064709 U | 4/1988 |
| JP | S63-293312 | 11/1988 |
| JP | 3-161511 A | 7/1991 |
| JP | 04-008582 | 1/1992 |
| JP | 4-241115 A | 8/1992 |
| JP | 04-371148 | 12/1992 |
| JP | 07-313549 | 12/1995 |
| JP | 8-027533 A | 1/1996 |
| JP | 8-027653 A | 1/1996 |
| JP | 10-506586 T | 6/1998 |
| JP | 2001-055623 A | 2/2001 |
| JP | 2001-123088 A | 5/2001 |
| JP | 2001-170108 | 6/2001 |
| JP | 2002-138322 A | 5/2002 |
| JP | 2002-515926 T | 5/2002 |
| JP | 2005-211136 | 8/2005 |
| WO | WO 96/10380 | 4/1996 |
| WO | WO 96/13391 | 5/1996 |
| WO | WO 98/02609 | 1/1998 |
| WO | WO 99/27876 A1 | 6/1999 |
| WO | WO 00/38915 | 7/2000 |
| WO | WO 03/035948 A1 | 5/2003 |
| WO | WO 04/001004 A2 | 12/2003 |
| WO | WO 2005/045894 | 5/2005 |
| WO | WO 2007/032710 | 3/2007 |

OTHER PUBLICATIONS

Form PCT/ISA/237 (Written Opinion of the International Searching Authority) dated Mar. 17, 2006.

Form PCT/IPEA/409 (International Preliminary Report on Patentability) dated Sep. 6, 2007.

Office Action issued in the corresponding Japanese Patent Application No. 2008-529944 dated Mar. 9, 2010, and an English Translation thereof.

Office Action issued Nov. 9, 2010 in corresponding JP Application No. 2008-529944 and English translation thereof.

Supplemental European Search Report dated Aug. 18, 2011, issued in the corresponding European Application No. 05783930.0-1219.

* cited by examiner

ABSORBENT ARTICLES AND LAMINATES CONTAINING A BONDING PATTERN

TECHNICAL FIELD

The present invention refers to an absorbent hygiene article such as a diaper, a pant diaper, a sanitary napkin, an incontinence guard etc., said article comprising components that are joined together by a bonding pattern. The invention further refers to laminates formed from two or more web material layers joined together by a bonding pattern and which are, used in any of the following disposable articles: absorbent hygiene articles, wipes, surgical drapes, surgical gowns, protective clothing, bed protection linings or the like.

BACKGROUND

Absorbent personal care articles of the above mentioned kind comprise a plurality of components, like different layers of material, such as inner and outer coversheets, absorbent structures, liquid transfer layers arranged between the inner coversheet and the absorbent structure, waist bands, side panels etc, and other components like elastic elongated members forming leg and waist elastics, fastening members like tape tabs, hook-and-loop fasteners etc. that are joined to other components by gluing, thermobonding or welding, especially ultrasonic welding or laser welding. Material layers can either be joined together to form a laminate or be joined in a side-by-side relationship with an overlap to form a seam there between.

Laminates formed from two or more web material layers, especially fibrous layers, foam layers, plastic films and combinations thereof, joined together by gluing, thermobonding or welding, especially ultrasonic welding or laser welding, are in absorbent personal care articles, used in wipes, surgical drapes, surgical gowns, protective clothing etc.

Thermobonding and welding in the above cases are often performed using a pattern roll so that a bonding pattern is formed. The visual effect provided by the bonding pattern is however often rather faint. This makes it difficult to control the quality of the bonding pattern in a process.

OBJECT AND SUMMARY

One object is to provide an absorbent article comprising at least two components that are joined together by a bonding pattern, provided by thermobonding or welding, wherein the bonding pattern is made easily visible for decorative purposes and/or for process and quality control purposes. This has been achieved by the fact that said bonding pattern has colour-changing properties triggered by heat and/or pressure exerted during the bonding process, said colour-changing properties being either irreversible or reversible.

In one aspect at least one of said components contains a thermochromic pigment or a thermochromic pigment is applied between said components. The thermochromic pigment is according to one embodiment in thermochromic fibres.

In another aspect at least one of said components contains a pigment that changes colour when exerted to a pressure exceeding a selected value. According to one embodiment the pigment is microencapsulated, wherein the pigment is released when exerted to a pressure exceeding said selected value.

In a further aspect said components comprise at least two web material layers that are joined together by a bonding pattern having a different colour than the rest of said material layers. According to one embodiment said web material layers are joined to form a laminate forming at least a part of one or more of the following components of the article: an inner coversheet, an outer coversheet, a liquid transfer layer arranged between the inner coversheet and an absorbent structure, a combined inner coversheet and liquid transfer layer. According to a further embodiment said material layers are joined in an overlapping side-by-side relationship to form a seam there between.

In a still further aspect at least one of said components is an elastic member joined to a web material layer.

According to one embodiment the bonding pattern is a welding pattern, such as an ultrasonic or laser welding pattern. In another embodiment the bonding pattern is a thermobonding pattern.

In a still further embodiment the bonding pattern is an adhesive bonding pattern. In this case the hot adhesive, when applied on a component containing thermochromic pigment or fibers, will trigger a colour change of said thermochromic pigment or fibers corresponding to the pattern of the deposited adhesive.

According to one embodiment the thermochromic pigments or fibers change colour at a temperature of between 45 and 150° C., preferably between 50 and 130° C., more preferably between 50 and 120° C. and most preferably between 60 and 120° C.

According to a further embodiment the thermochromic pigments or fibers change colour at a temperature of at least 10° C., preferably at least 20° C. lower than and most preferably between 10-30° C. lower than the temperature exerted to components during the process of joining them together with said bonding pattern. As the pigment or fiber preferably should change colour only at the bonding step and not at other process steps including during high temperature transport and storage of the articles, the trigger temperature, at which the colour change occurs, should be relatively high and higher than the temperatures normally occurring during other process steps and during transport and storage.

In a still further embodiment the disclosure refers to a laminate formed from two or more web material layers joined together by a bonding pattern, wherein said bonding pattern has colour-changing properties triggered by heat and/or pressure exerted during the bonding process, said colour-changing properties being either irreversible or reversible. According to one embodiment at least one of said web material layers of the laminate contains a thermochromic pigment. In a still further embodiment the thermochromic pigment is comprised in thermochromic fibres.

In an alternative embodiment at least one of said web material layers of the laminate contains a pigment that changes colour when exerted to a pressure exceeding a selected value or that said pigment is applied between said components. Said pigment may be microencapsulated, wherein the pigment is released when exerted to a pressure exceeding said selected value.

In a still further embodiment a thermochromic pigment, thermochromic fibres and/or a pressure-sensitive pigment is applied between at least two material layers of the laminate.

According to one embodiment the bonding pattern is a welding pattern, such as an ultrasonic or laser welding pattern. According to another embodiment the bonding pattern is a thermobonding pattern.

In a still further embodiment the bonding pattern is an adhesive bonding pattern. In this case the hot adhesive, when applied on a web material containing thermochromic pigment or fibers, will trigger a colour change of said thermochromic pigment or fibers corresponding to the pattern of the deposited adhesive.

According to one embodiment the thermochromic pigments or fibers change colour at a temperature of between 45 and 150° C., preferably between 50 and 130° C., more preferably between 50 and 120° C. and most preferably between 60 and 120° C.

According to a further embodiment the thermochromic pigments or fibers change colour at a temperature of at least 10° C., preferably at least 20° C. lower than and most preferably between 10-30° C. lower than the temperature exerted to web materials during the process of joining them together with said bonding pattern. As the pigment or fiber preferably should change colour only at the bonding step and not at other process steps and during high temperature transport and storage of thelamiates, the trigger temperature, at which the colour change occurs, should be relatively high and higher than the temperatures normally occurring during other process steps and during transport and storage.

The laminate may be used in any of the following articles: laminate is used in any of the following disposable articles: absorbent hygiene articles, wipes, surgical drapes, surgical gowns, protective clothing, bed protection linings or the like.

According to one aspect the two or more web material layers are joined in-line with further manufacturing steps correlating with said articles.

BRIEF DESCRIPTION OF DRAWINGS

Embodiments of the invention will be described in the following in greater detail by way of examples and with reference to the accompanying drawings, in which.

DEFINITIONS

Absorbent Article

Figure 1:
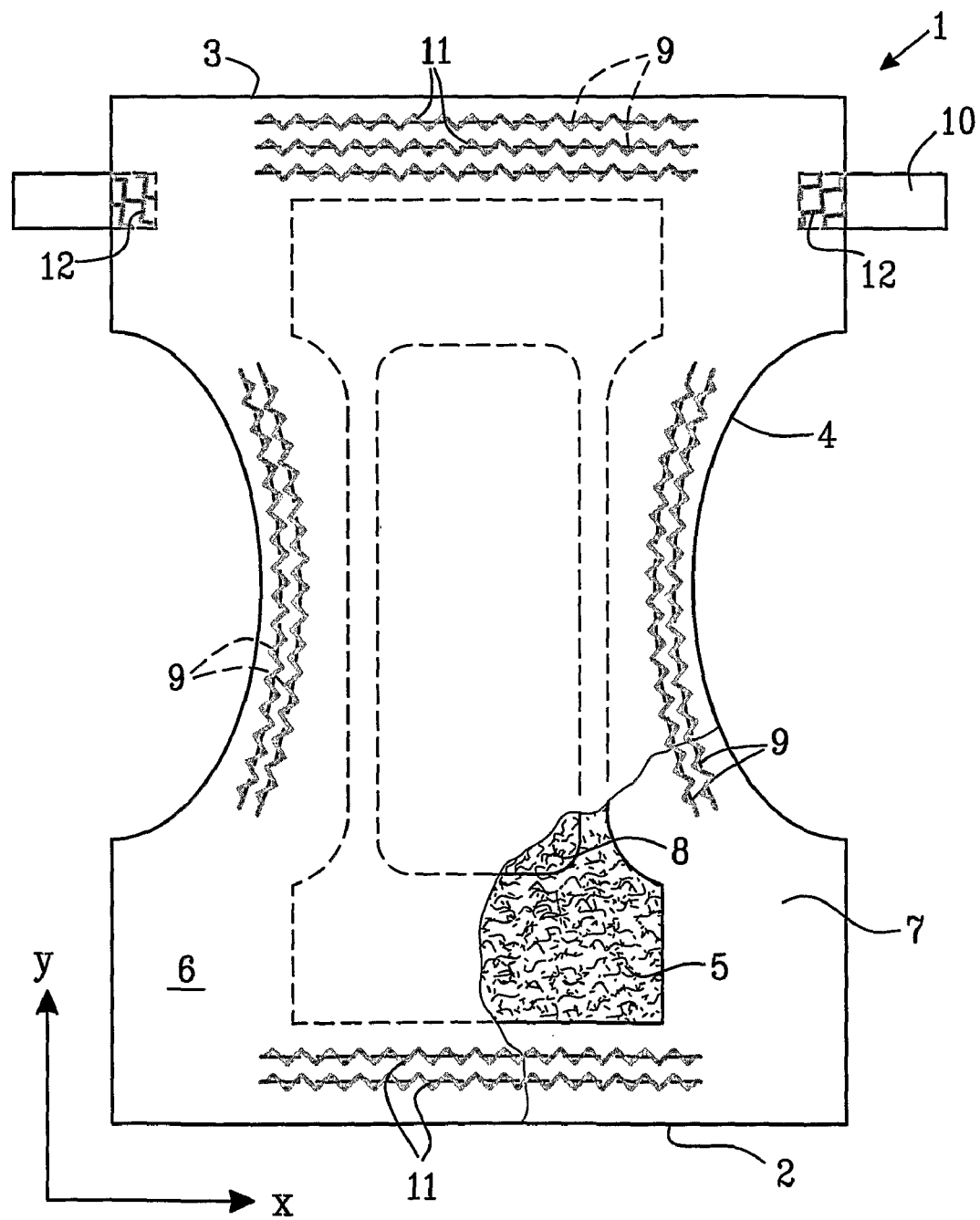
FIG. 1 is a schematic perspective view of a diaper.

The term "absorbent article" refers to products that are placed against the skin of the wearer to absorb and contain body exudates, like urine, feces and menstrual fluid. The invention mainly refers to disposable absorbent articles, which are articles that are not intended to be laundered or otherwise restored or reused as an absorbent article after use.

Inner Liquid Permeable Cover

The inner liquid permeable cover forms the inner cover of the absorbent article and in use is placed in direct contact with the skin of the wearer. The inner liquid permeable cover can comprise a nonwoven material, e.g. spunbond, meltblown, carded, hydroentangled, wetlaid etc. Suitable nonwoven materials can be composed of natural fibers, such as woodpulp or cotton fibres, manmade fibres, such as polyester, polyethylene, polypropylene, viscose etc. or from a mixture of natural and manmade fibres. The inner liquid permeable cover material may further be composed of tow fibres, which may be bonded to each other in a bonding pattern, as e.g. disclosed in EP-A-1 035 818. Further examples of inner liquid permeable cover materials are porous foams, apertured plastic films, laminates of nonwoven/nonwoven or film/nonwoven etc. The layers in a laminate may be bonded to each other by gluing, by ultrasonic welding, laser welding or by thermobonding. The materials suited as inner liquid permeable cover materials should be soft and non-irritating to the skin and be readily penetrated by body fluid, e.g. urine or menstrual fluid. The inner liquid permeable cover may further be different in different parts of the absorbent article.

Outer Liquid Impermeable Cover

The outer liquid impermeable cover forms the outer cover of the absorbent article at least on the core area thereof. The outer liquid impermeable cover can comprise a thin plastic film, e.g. a polyethylene or polypropylene film, a nonwoven material coated with a liquid impervious material, a hydrophobic nonwoven material, which resists liquid penetration, or a laminate, e.g. of a plastic film and a nonwoven material. The outer liquid impermeable cover material may be breathable so as to allow vapour to escape from the absorbent structure, while still preventing liquids from passing through. Examples of breathable outer liquid impermeable cover materials are porous polymeric films, nonwoven laminates from spunbond and meltblown layers, laminates from porous polymeric films and nonwoven materials, Absorbent Structure The "absorbent structure" is the absorbent structure disposed between the two covers of the absorbent article. The absorbent structure can be of any conventional kind. Examples of commonly occurring absorbent materials are cellulosic fluff pulp, tissue layers, highly absorbent polymers (so called superabsorbents), absorbent foam materials, absorbent nonwoven materials or the like. It is common to combine cellulosic fluff pulp with superabsorbent polymers in an absorbent structure. Superabsorbent polymers are water-swellable, water-insoluble organic or inorganic materials capable of absorbing at least about 20 times its weight of an aqueous solution containing 0.9 weight percent of sodium chloride. Organic materials suitable for use as a superabsorbent material can include natural materials such as polysaccharides, polypeptides and the like, as well as synthetic materials such as synthetic hydrogel polymers. Such hydrogel polymers include, for example, alkali metal salts of polyacrylic acids, polyacrylamides, polyvinyl alcohol, polyacrylates, polyacrylamides, polyvinyl pyridines, and the like. Other suitable polymers include hydrolyzed acrylonitrile grafted starch, acrylic acid grafted starch, and isobutylene maleic anhydride copolymers and mixtures thereof. The hydrogel polymers are preferably lightly crosslinked to render the material substantially water insoluble. Preferred superabsorbent materials are further surface crosslinked so that the outer surface or shell of the superabsorbent particle, fiber, flake, sphere, etc. possesses a higher crosslink density than the inner portion of the superabsorbent. The superabsorbent materials may be in any form suitable for use in absorbent composites including particles, fibers, flakes, spheres, and the like.

A high absorption capacity is provided by the use of high amounts of superabsorbent material. For an absorbent structure comprising a matrix of hydrophilic fibers, such as cellulosic fibers, and superabsorbent material, the proportion of superabsorbent material is preferably between 10 and 90% by weight, more preferably between 30 and 70% by weight.

It is conventional in absorbent articles to have absorbent structures comprising layers of different properties with respect to liquid receiving capacity, liquid distribution capacity and storage capacity. The thin absorbent bodies, which are common in for example baby diapers and incontinence guards, often comprise a compressed mixed or layered structure of cellulosic fluff pulp and superabsorbent polymers. The size and absorbent capacity of the absorbent structure may be varied to be suited for different uses such as for infants or for adult incontinent persons.

Acquisition Layer

A so called acquisition layer may be arranged between the inner liquid permeable cover and the absorbent structure. The acquisition layer is adapted to quickly receive and temporarily store discharged liquid before it is absorbed by the underlying absorbent structure. Such acquisition distribution layers are well known in the art and may be composed of porous fibrous waddings or foam materials. They may further be joined to the inner liquid pervious cover by gluing or by a bonding pattern created by ultrasonic or laser welding or by thermobonding.

Thermochromic Pigments

Thermochromic pigments are organic compounds that effectuate a reversible or irreversible colour change when a specific temperature threshold is crossed. A thermochromic pigment basically comprises three main components: (i) an electron donating colouring organic compound, (ii) an electron accepting compound and (iii) a solvent reaction medium determining the temperature of the colouring reaction to occur.

A thermochromic particulate material which may be used may be prepared from particles of a non-thermoplastic resin having enclosed therein the three components of electron-donating chromogenic substance, electron-accepting substance and solvent by coating the particles with a hydrophilic high-molecular-weight compound. The thermochromic particulate material, when incorporated into a vinyl chloride plastisol, remains free of the influence of the plasticizer, stabilizer, lubricant or the like contained in the plastisol and retains very high stability even when heated.

The process for preparing a molded product of thermochromic polyvinyl chloride is characterized by incorporating a thermochromic particulate material into a vinyl chloride plastisol comprising a vinyl chloride resin, plasticizer, stabilizer, lubricant and filler. Thereafter molding the resulting mixture. The thermochromic particulate material being prepared from particles of a non-thermoplastic resin having encapsulated therein the three components of electron-donating chromogenic substance, electron-accepting substance and solvent by coating the particles with a hydrophilic high-molecular-weight compound.

A molded thermochromic polyvinyl chloride material can thereby be prepared which reliably undergoes a reversible color change with a change of temperature. A material like this becomes skin-colored when the temperature rises beyond about 40° C. The color change is reversible. This is further described in U.S. Pat. No. 4,826,550.

Such thermochromic pigments and the mechanism bringing about the temperature triggered colour change to occur are well-known in the art and are for example described in U.S. Pat. No. 4,826,550 and U.S. Pat. No. 5,197,958.

Thermochromic Fibres

Thermochromic or, as they also are called, temperature sensitive colour changing fibres are known from the textile field to be used in clothing, sport equipment etc. The fibres are either produced by blending a thermochromic pigment in the base resin from which the fibres are to be produced, for example a polyolefin, such as polyethylene or polypropylene, polyester, polyvinyl alcohol etc. or by using a thermochromic colouring liquid for the fibers. The production of temperature sensitive colour-changing fibres are disclosed in for example JP2002138322 and JP2001123088. The fibres change colour at a selected temperature. The change of colour is either reversible or irreversible.

An example of a fiber which can be used is a thermochromic fiber which is partly characterized in that the flexural modulus of elasticity of a base resin is within the range of 300-1,500 MPa in the temperature-sensing color-changing fiber. The fiber is formed by melt blending a thermally color-changing pigment in a dispersed state in the base resin of a polyolefin resin and/or the polyolefin resin blended with a thermoplastic resin. This fiber is earlier used in the textile field. The inventors have found that fibers with this characteristic may also be suited for use in absorbent articles, especially diapers. The fiber is further described in JP 2002-138322.

In another embodiment the thermochromic fiber is a thermosensitive color-changing acrylic synthetic fiber. Such fibers may be constituted of a plurality of long fibers or short fibers of a thermosensitive color-changing synthetic acrylic fiber having 1-100 µm outer diameter of monofilament. The fibers may be formed by dispersing 0.5-40 wt. % of a thermosensitive pigment containing essential three ingredients of (A) an electron donating coloring organic compound, (B) an electron-accepting compound and (C) a reaction solvent determining the occurrence temperature of a coloring reaction of the ingredients A and B. This is described in more detail in JP 2001-055623.

Another thermochromic fiber is a conjugate fiber which is excellent in reversible color changeability, brightness and durability. It may be produced by using a (1) thermal color changing polyester composed of a thermal color changing material-containing thermoplastic polyester and (2) a fiber-forming polyester in which ≧50 mol % of an acid component is terephthalic acid; 0-50 mol % thereof is isophthalic acid and ≧70 mol % of a diol component is composed of butanediol and/or hexanediol are subjected to melt conjugate spinning. The resultant yarn is then drawn to afford the objective fiber which is conjugate fiber, containing a part composed of the component (1) joined to a part composed of the component (2) and having ≧1.5 g/denier fiber strength, ≦80% fiber elongation and ≦25% shrinkage factor in boiling water. This is further described in JP 4241115.

Another fiber which is excellent in friction durability and mechanical characteristics which may be suitable can be achieved by using a low-melting thermoplastic resin containing a temperature-sensitive color changing granular substance as a core component and a high-melting thermoplastic resin as a sheath component at a specific ratio.

The fiber is obtained by mixing an acid developing substance (e.g. 3,3'-dimethoxyfluoran) with an acidic substance (e.g. phenol) and a solvent (e.g. octyl alcohol), granulating the resultant mixture and carrying out conjugate spinning of a thermoplastic resin (e.g. polypropylene), having ≦230° C. melting point and containing 1-40 wt. % resultant temperature-sensitive color changing granular substance. The granules having 1-50 µm grain diameter and ≧200° C. heat resistance as a core component and a thermoplastic resin (e.g. nylon) having ≦280° C. melting point as a sheath composition at (1/9)-(9/1) weight ratio of core component:sheath component, having a smooth surface and excellent in mechanical characteristics with a high level of temperature-sensitive color changing function. This method is further described in JP 3161511.

The temperature sensitive pigment used in the thermochromic fibers has preferably an average particle size of 0.5-50 µm, preferably 0.5-30.0, even more preferably µm 0.5-15.0 µm measured by appropriate ASTDM standard method.

The thermosensitive pigment may preferably be of a microcapsule type which is known in the art of thermosensitive pigments.

Pressure Activated Pigments

A pressure activated pigment develops or changes colour when exerted to a pressure exceeding a certain threshold value. The pigment may be encapsulated in microcapsules, optionally with a developing agent, said microcapsules burst when exerted to a certain pressure, at which the pigment is activated and released.

Laminate

The term laminate as used herein refers to a web material composed of two or more web material layer, such as fibrous layer, foam layers, plastic films and/or combinations thereof. The different layers are joined together by adhesive, thermobonding or by ultrasonic or laser welding. The web material layers may be inelastic, elastic or combinations thereof.

DESCRIPTION OF PREFERRED EMBODIMENTS

The absorbent article shown in FIG. 1 is in the form of a diaper 1 having a longitudinal, y, and a transverse direction, x, and comprises, as seen in its longitudinal direction, a front portion 2, a back portion 3 and a crotch portion 4 there between. In its most common form the diaper comprises an absorbent structure 5 and a cover enclosing the absorbent structure. Said cover comprises an inner liquid pervious cover 6 on the wearer facing side of the absorbent structure 5 and an outer liquid impervious cover 7 on the garment facing side of the absorbent structure. The inner liquid pervious cover 6 is often referred to as topsheet, while the outer liquid impervious cover 7 is often referred to as backsheet. An acquisition layer 8 is arranged between the inner liquid pervious cover 6 and the absorbent structure 5.

The inner cover 6 and the outer cover 7 extend outward beyond the peripheral edges of the absorbent structure 5 and have their inner surfaces bonded to each other, e.g. by gluing, thermobonding or welding by heat or ultrasonic. The inner and outer cover materials may further be bonded, e.g. by adhesive, to the absorbent structure.

The areas of the article adjacent the leg openings are along the longitudinal side edges provided with elongated elastic members or elastic threads 9 which are bonded between the inner cover 6 and the outer cover 7 material layers in a stretched condition so as to provide elasticized leg openings of the diaper. Corresponding elastic members 9 are arranged to extend in the transverse, x, direction in the front 2 and back portion 3 adjacent the transverse side edges forming the waist opening of the diaper.

The back portion 3 is provided with fasteners 10 attached thereto. The fasteners are intended to be fastened to the front region of the article to form a pant-like shape. The fasteners 10 may be in the form of adhesive tapes or hook elements adapted to attach to a loop material, for example in the form of a nonwoven material forming the outer coversheet of the diaper.

In FIG. 1 it is shown that the elastic threads 9 are bonded between the inner and outer cover materials 6 and 7 by a bonding pattern 11 provided by thermobonding, ultrasonic welding, laser welding or the like. The fasteners 10 are bonded to the outer cover 7 or between the outer and inner covers 7 and 6 by a corresponding bonding pattern 12. The bonding patterns 11 and 12 are visualized by having a colour that is different from the surrounding portions of the article. This visualization of the bonding pattern may serve different aspects, such as a decoration, as a quality control of the bonding or a combination of both aspects.

Visualization of the bonding pattern may be provided in different ways. One way is by the incorporation of a thermochromic pigment in at least those parts of a component that is intended to be bonded to another component. For the article in FIG. 1 the thermochromic pigment may thus be incorporated in any of the following components: the inner cover 6, the outer cover 7 and the fasteners 10. The thermochromic pigment may alternatively be applied between the components that are to be bonded together.

This thermochromic pigment is preferably colourless, or the same colour as the surrounding material, below a certain temperature, which preferably exceeds normal room, transport and storage temperatures and also lower than the temperatures to which the articles are exerted during manufacturing, except for the bonding step. When a specific temperature threshold is crossed the thermochromic pigment change colour and becomes visible and in contrast to the surrounding material. This temperature threshold should be slightly below the temperature that the components are exerted to by the bonding equipment during the bonding process. "Slightly below" in this context means at least 10° C., preferably between 10 and 30° C., lower than said temperature to which the components are exerted during the bonding process.

A suitable temperature threshold can be in the interval 45 and 150° C., preferably between 50 and 130° C., more preferably between 50 and 120° C. and most preferably between 60 and 120° C. As described above the choice of solvent reaction medium of the thermochromic pigment determines the temperature of the colouring reaction to occur. This is for example described in U.S. Pat. No. 4,826,550 and U.S. Pat. No. 5,197,958. The components of the thermochromic pigment may be encapsulated to form microcapsules. The change of colour of the thermochromic pigment after having crossed the selected temperature threshold should be irreversible in case a permanent visualization of the bonding pattern is desired. In case the visualization is for quality control purposes in connection to the bonding process, it is possible to have a reversible thermochromic pigment.

Another way to visualize the bonding pattern is by means of thermochromic fibres, which simply are fibres having incorporated therein a thermochromic pigment. A description of fibers having incorporated therein such thermochromic pigments can be found in any of the following Japanese published patent applications: JP 2002-138322, JP 2001-123088, JP 2001-055623 and JP 08-027533. The thermochromic pigment may be incorporated in the base resin of the fibers in the form of microcapsules or as a colouring liquid for the fibres.

The thermochromic fibers may be incorporated in at least those parts of a component that is intended to be bonded to another component or may alternatively be applied between the components that are to be bonded together.

The entire fibre may be coloured by the thermochromic pigment, or the fibre may be of a bicomponent type, wherein either the core or the outer casing of the fibre is provided with the thermochromic pigment. The change of colour should occur at the same temperature interval as described above and be irreversible in case a permanent visualization of the bonding pattern is desired, otherwise it is possible to use reversible thermochromic fibres.

A still further way to visualize the bonding pattern is by means of a pressure sensitive pigment that changes colour when exerted to a pressure exceeding a selected threshold value. This pressure sensitive pigment can be microencapsulated, wherein the colour changing pigment is activated and released when exerted to a pressure exceeding said selected threshold value, such as when exerted to a bonding step under simultaneous compression. This selected threshold value should exceed the pressures exerted to the article during for example transport and storage and during other process steps than compressive bonding.

Figure 2:
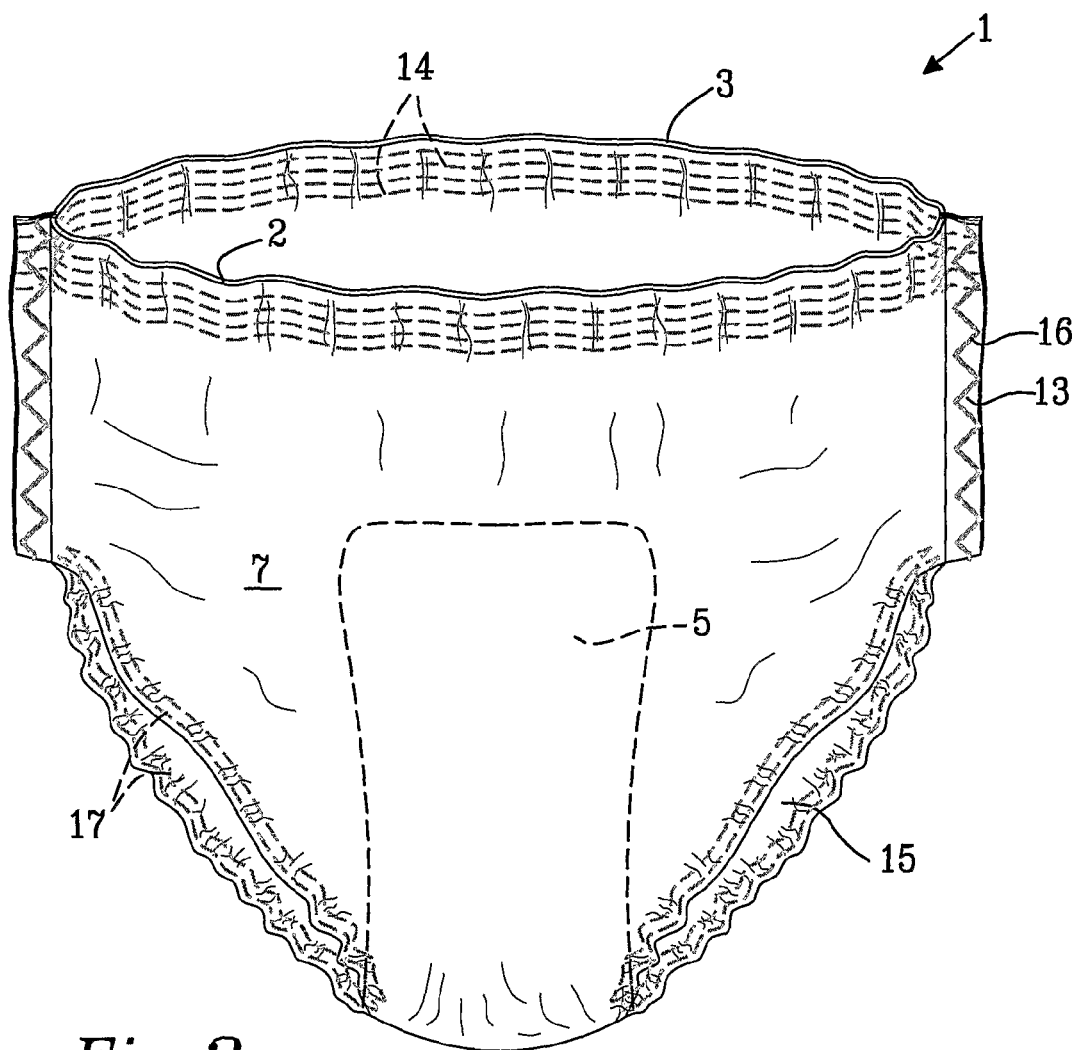
FIG. 2 is a schematic perspective view of a pant diaper.

FIG. 2 shows a so called pant diaper in which the front and back portions 2 and 3 are joined to each other along their longitudinal side edges thereof forming side seams 13, to define a waist-opening 14 and a pair of leg-openings 15. The front and back portions 2 and 3 are joined along said side seams 13, for example by adhesive, ultrasonic welding or laser welding, thermobonding or the like. The front and back portions 2 and 3 may be joined along said side seams with the inner cover 6 facing inwards, as is shown in the drawings. Alternatively they are joined in an overlapped manner with the inner cover 6 of either the front or back portion facing the outer cover 7 of the opposite region.

In FIG. 2 it is shown that the side seams 13 are bonded by a visual bonding pattern 16, which may be an ultrasonic or laser welding pattern or a thermobonding pattern. Visualization is provided by a thermochromic pigment, thermochromic fibres or a pressure sensitive pigment in the same way as described above with reference to the diaper in FIG. 1.

The waist area, at least a part of the leg opening area and the side areas adjacent the side seams 13 are elasticized. The elastification is usually accomplished by a plurality of elastic members, such as elastic threads 17, contractably affixed in a stretched condition between the outer cover 7 and the inner cover 6. Alternatively elastic materials, such as an elastic laminate, may be used to form the chassis of the article in those areas where elasticity is desired.

In FIG. 2 the elastic threads 17 are visualized by having a thermochromic pigment, thermochromic fibres or a pressure-sensitive pigment incorporated therein, which change colour during the bonding process when the elastic threads 17 are bonded to the inner and outer covers 6 and 7.

Figure 3:
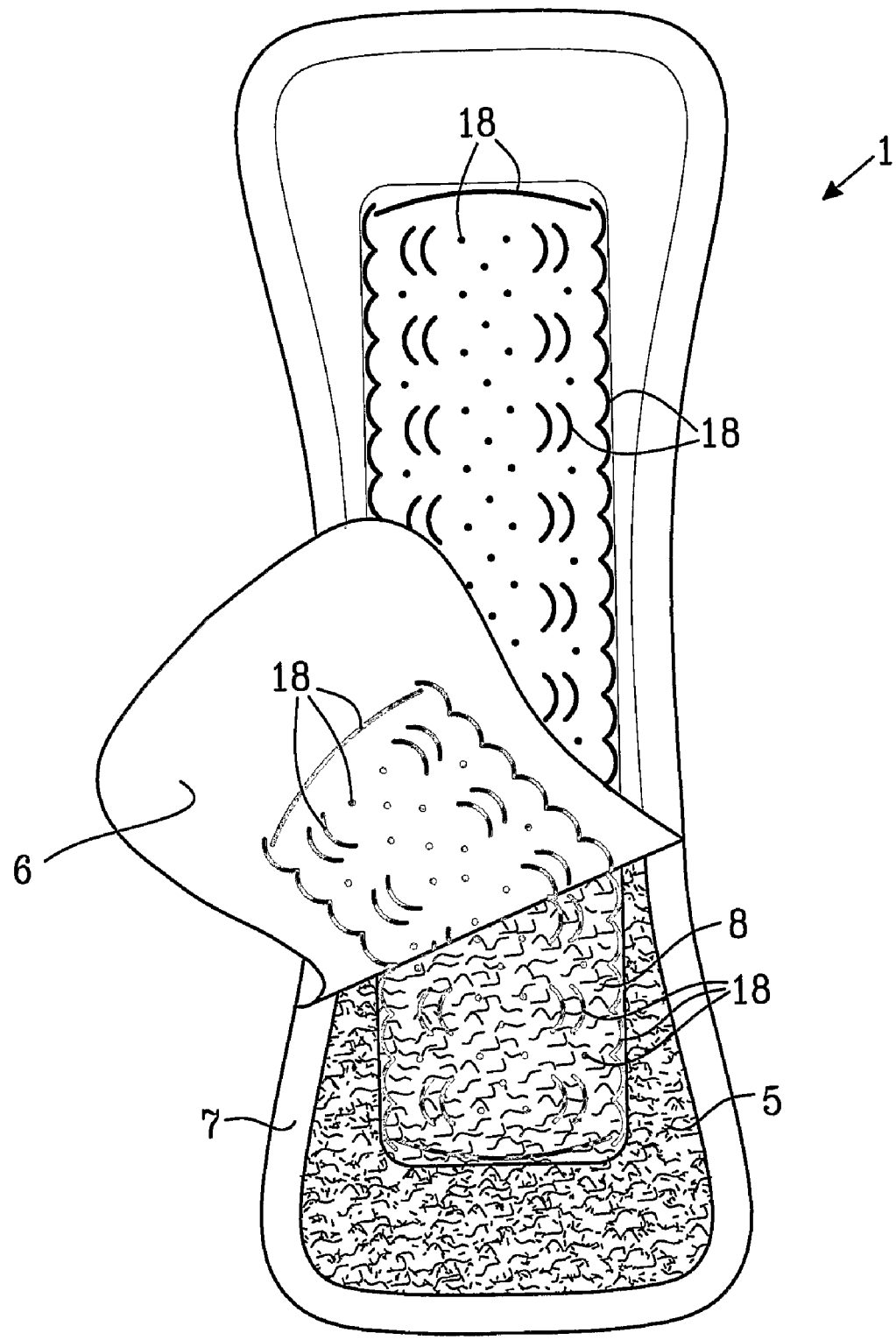
FIG. 3 is a schematic view of a sanitary napkin or incontinence guard.

FIG. 3 shows a further embodiment in the form of an incontinence guard or sanitary napkin intended to be worn in the panties of a wearer. The article comprises an acquisition layer 8 arranged between the inner cover 6 and the absorbent structure 5. The acquisition layer 8 is bonded to the inner cover 6 with a bonding pattern 18 provided by thermobonding, ultrasonic welding or laser welding. One or both of the inner cover and acquisition layer contains thermochromic pigment, thermochromic fibres or pressure sensitive pigment at least in those parts of the layers that are intended to be bonded together. Alternatively the thermochromic pigment, thermochromic fibres or pressure sensitive pigment are applied between the layers that are going to be bonded together.

The thermochromic/pressure-sensitive pigments/fibres may be incorporated substantially homogeneously in an entire material layer and mixed with other fibers in the layer. Alternatively they are incorporated only in parts of a layer. An appropriate amount of the thermochromic fibres in for example an inner coversheet, an acquisition layer, an absorbent structure or a layer in an absorbent structure or an outer coversheet, is at least 1% by weight, preferably at least 10% by weight and more preferably from 20 to 70% by weight based on the weight of said fibrous layer in areas in which said thermochromic fibres are distributed. Thus if the thermochromic fibres are distributed in only part of the layer, the weight-% should be based on the weight of that part of the layer.

A further alternative is to apply the thermochromic/pressure-sensitive pigments/fibres between the layers that are going to be bonded together.

One problem that may occur in processes where for example the inner cover 6 and/or the acquisition layer 8 is exerted to an additional bonding process in order to bond the material before being joined to other components. If the layer contains thermochromic pigment/fibres which have an irreversible colour change, this colour change could be triggered by any heat activated bonding process and remain as a permanent colour change of that material layer. This problem would however be avoided by using other bonding techniques for bonding the individual layers, such as resin bonding, needling techniques, hydroentangling etc.

The absorbent articles shown in the drawings are only examples of some common types of personal care absorbent articles and the invention may be applied to any type of absorbent articles falling under the definition given above.

The invention is also applicable to laminates of different types, wherein two or more web material layers, especially fibrous layers, foam layers, plastic films or the like, are joined together by thermobonding or ultrasonic welding or laser welding. Such laminates may besides in absorbent personal care articles, be used in wipes, surgical drapes, surgical gowns, protective clothing etc. Visualization of bonding patterns, either permanent or temporary visualization, may in all these types of laminates be provided by the incorporation of thermochromic pigments, thermochromic fibres or pressure sensitive pigments in one or more of the material layers or between the material layers, in the manner described above with reference to the absorbent articles.

The invention claimed is:

1. An absorbent article for hygiene purposes, said article comprising components that are joined together by a bonding pattern, said components are selected from:
   i) different layers of material,
   ii) elastic elongated members joined to other components of the article, and
   iii) fastening members joined to other components of the article,
wherein said components at the bonding pattern have colour-changing properties triggered by heat or pressure exerted during the bonding process, wherein said pigment is microencapsulated, wherein the pigment is released when exerted to a pressure exceeding said selected value.

2. The absorbent article as claimed in claim 1, wherein said components comprise different side panels that are joined together at the edges therefore by a bonding pattern at a side seam.

3. The absorbent article as claimed in claim 2, wherein said body panels are joined in an overlapping side-by-side relationship to form a seam there between.

4. The absorbent article as claimed in claim 1, wherein said components comprise an elastic member joined to a web material layer of the article.

5. The absorbent article as claimed in claim 1, wherein said components comprise a fastening tab joined to a web material layer of the article.

6. The absorbent article as claimed in claim 5, wherein the fastening tab is a tape tab or a hook and loop fastener.

7. The absorbent article as claimed in claim 1, wherein said bonding pattern is a welding pattern.

8. The absorbent article as claimed in claim 7, wherein the welding pattern is an ultrasonic or a lesser welding pattern.

9. The absorbent article as claimed in claim 1, wherein said bonding pattern is a thermobonding pattern.

10. The absorbent article as claimed in claim 1, wherein said bonding pattern is an adhesive bonding pattern.

11. The absorbent article as claimed in claim 1, wherein said components are joined in-line with further manufacturing steps correlating with said article.

12. The absorbent article as claimed in claim 1, wherein the article is a diaper, a pant diaper, a sanitary napkin, or an incontinence guard.

13. The absorbent article as claimed in claim 1, wherein said different layers of material are joined to form a laminate forming at least a part of one or more of the following components of the article: an inner coversheet, an outer coversheet, a liquid acquisition layer arranged between the inner coversheet and an absorbent structure, and a combined inner coversheet and liquid acquisition layer.

14. The absorbent article as claimed in claim 1, wherein said components comprise a fastening tab joined to a side panel of the article.

15. An absorbent article for hygiene purposes, said article comprising components that are joined together by a bonding pattern, said components are selected from:
   i) different layers of material,
   ii) elastic elongated members joined to other components of the article, and
   iii) fastening members joined to other components of the article, wherein said components at the bonding pattern have colour-changing properties triggered by heat or pressure exerted during the bonding process, wherein the colour-changing properties are reversible.

16. The absorbent article as claimed in claim 15, wherein said different layers of material are joined to form a laminate forming at least a part of one or more of the following components of the article: an inner coversheet, an outer coversheet, a liquid acquisition layer arranged between the inner coversheet and an absorbent structure, and a combined inner coversheet and liquid acquisition layer.

17. An absorbent article for hygiene purposes, said article comprising an elastic thread joined to other components of the article by a bonding pattern,
   wherein said elastic thread or other components at the bonding pattern have colour-changing properties triggered by heat or pressure exerted during the bonding process.

* * * * *